United States Patent [19]
Yamaguchi et al.

[11] Patent Number: 6,090,598
[45] Date of Patent: *Jul. 18, 2000

[54] ENZYMATIC PROCESS FOR INTERESTERIFICATION OF FATS AND OILS USING DISTILLATION

[75] Inventors: Kotaro Yamaguchi; Masayuki Fukazawa; Tadahisa Shimoda; Tsugio Izumi, all of Osaka-fu, Japan

[73] Assignee: Fuji Oil Company, Limited, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/791,810

[22] Filed: Jan. 30, 1997

[51] Int. Cl.$^7$ .................................. C12P 7/64; C12P 7/62
[52] U.S. Cl. ........................... 435/134; 435/135; 426/607
[58] Field of Search ..................... 435/134, 135; 426/607

[56] References Cited

U.S. PATENT DOCUMENTS

| | | | |
|---|---|---|---|
| 2,704,764 | 3/1955 | Mattikow et al. | 435/134 |
| 3,915,872 | 10/1975 | Sturwold | 252/49 |
| 4,985,358 | 1/1991 | Sawamure et al. | 435/134 |
| 5,190,868 | 3/1993 | Kokusho et al. | 435/134 |
| 5,424,090 | 6/1995 | Okawauchi et al. | 426/607 |

*Primary Examiner*—Irene Marx
*Attorney, Agent, or Firm*—Wenderoth, Lind & Ponack, L.L.P.

[57] ABSTRACT

There is disclosed a process for modifying fats and oils by an interesterification reaction to efficiently increase concentrations of the desired triglycerides. In the process, a step for subjecting a fat or oil to an interesterification reaction with a fatty acid or its lower alcohol ester in the presence of an enzyme catalyst and then a step for removing the fatty acid or its lower alcohol ester by distillation are repeated in multiple stages. The process is characterized by leaving the fat or oil and a feedstock fatty acid or its ester selectively in the distillation steps preceding the one in the final stage. According to this process, the amount of the fatty acid or its ester to be used can be reduced and the formation of by-products can be inhibited, thereby enabling to increase concentrations of the desired triglycerides more efficiently than conventional multistage interesterification processes.

3 Claims, No Drawings

6,090,598

ENZYMATIC PROCESS FOR INTERESTERIFICATION OF FATS AND OILS USING DISTILLATION

FIELD OF THE INVENTION

The present invention relates to a process for interesterification of fats and oils.

BACKGROUND OF THE INVENTION

Properties of fats and oils can be modified by an interesterification reaction of the fats and oils with a fatty acid or lower alcohol ester thereof (hereinafter referred to as "fatty reactant") in the presence of an enzyme to introduce a specific fatty acid residue into triglycerides to increase a concentration of specific triglyceride molecular species. However, this reaction is an equilibrium reaction and, therefore, when a target concentration of the desired triglyceride molecular species is higher, a larger amount of an expensive feedstock fatty reactant is required. Then, after the reaction, the fats and oils are subjected to fractionation such as solvent fractionation to obtain the desired target concentration with a limited amount of a feedstock fatty reactant.

However, solvent fractionation requires large facilities and therefore high costs. In addition, from a safety viewpoint, to use a solvent should be minimized. Then, if a concentration of the desired triglyceride molecular species could be sufficiently increased only by an interesterification reaction with a limited amount of a feedstock fatty reactant but without any solvent fractionation, it would be desirable.

As for a process for improving a reaction efficiency of a fatty reactant, a multistage interesterification reaction has been known. However, any sufficient efficiency cannot be obtained by merely increasing the number of the stages. And, isomerization is caused by migration of triglycerides and diglycerides during a distillation step of one stage, which results in formation of undesirable by-products during the reaction in a subsequent stage. For example, in case of production of SOS-type hard butter from an oleic fat or oil and a stearic acid ester (S: stearic acid as a constituent fatty acid of a triglyceride, O: oleic acid as a constituent fatty acid of a triglyceride), an isomer SSO is formed and, in the reaction of the next stage, SSS is formed. Then, it is necessary to fractionate such by-products. In addition, problems such as deterioration of color due to heat history and lowering of stability to deterioration by oxidation are caused.

On the other hand, JP-A 5-219971 discloses a process for multistage interesterification of fats and oils, wherein a fatty reactant used in an interesterification reaction of one stage as such is fed to the reaction of the next stage to improve the reaction efficiency of the fatty reactant. However, such problems as by-products, deterioration of color and lowering of stability to deterioration by oxidation are not yet solved.

JP-B 3-69516 discloses a process for interesterification of fats and oils, wherein a fatty acid ester is separated from a reaction mixture and, after hydrogenation, it is returned to another reaction mixture.

However, to leave fats and oils together with a specific fatty reactant in a reaction mixture has not been known in the prior art.

OBJECTS OF THE INVENTION

The main object of the present invention is to provide an improved process for interesterification of fats and oils which can increase a concentration of the desired triglyceride molecular species, efficiently.

This object as well as other objects and advantages of the present invention will become apparent to those skilled in the art from the following description.

SUMMARY OF THE INVENTION

The present inventors have studied various interesterification reactions of fats and oils, intensively. As a result, it has been found that a concentration of the desired triglyceride molecular species can efficiently be increased without fractionation by carrying out distillation in such a manner that only fatty acids and/or their esters liberated from triglycerides due to interesterification which have boiling points lower than that of a feedstock fatty reactant to be introduced into triglycerides are distilled off with preventing distillation of the feedstock fatty reactant. This is quite different form conventional multistage interesterification processes because, in conventional processes, any fatty reactant in the reaction mixture is completely distilled off.

That is, according to the present invention, there is provided an improved process for interesterification of a fat or oil which comprises repeating a steps for subjecting the fat or oil to an interesterification reaction with a fatty reactant in the presence of an enzyme catalyst and then a step for removing the fatty reactant by distillation in multiple stages, wherein the improvement comprises leaving the fat or oil and a feedstock fatty reactant selectively in distillation steps preceding the one in the final stage.

DETAILED DESCRIPTION OF THE INVENTION

In the present invention, combination of the feedstock fat or oil with the feedstock fatty reactant should be selected so that only fatty acids and/or esters liberated from the feedstock fat or oil due to interesterification can selectively be distilled off as much as possible with preventing distillation of the feedstock fatty reactant. Then, in general, they should be selected so that fatty acids and/or esters liberated from the feedstock fat or oil have boiling points lower than that of the feedstock fatty reactant to be introduced into triglycerides.

In so far as the above requirement is met, any feedstock fat or oil can be used and examples thereof include vegetable oils such as sunflower oil, high oleic sunflower oil, safflower oil, high oleic safflower oil, soybean oil, rapeseed oil, olive oil, palm oil, sal fat, shea fat, coconut oil, palm kernel oil and the like and animal oils such as fish oils, cattle fat, lard and the like. They can be used alone or combination thereof. Synthetic glycerides such as MCT and trilaurin can be also used. Examples of the feedstock fatty reactant include fatty acids having 12 to 24 carbon atoms such as palmitic acid, oleic acid, behenic acid and their lower alcohol (having 1 to 4 carbon atoms) esters such as methyl and ethyl esters.

The interesterification reaction is carried out by using the above feedstock fat or oil and fatty reactant. The reaction per se can be carried out according to a known process. For example, an enzyme preparation prepared by immobilizing an enzyme or microbial cells having interesterification activity such as a lipase and the like according to a known method can be used as a catalyst.

The reaction mixture is distilled off according to a known method for distillation of a fatty reactant from fats and oils. In the present invention, distillation is carried out under such conditions that the feedstock fat or oil and the feedstock reactant are selectively left in a distillation step preceding the one in the final stage. Specifically, the distillation temperature can be selected so that the fatty acids and/or esters liberated from the feedstock fat or oil are distilled off as much as possible, while only the feedstock fat or oil and the feedstock fatty reactant substantially and selectively remain in a large amount.

This temperature is preferably lower than that for distilling off all the fatty acids and esters in the reaction mixture, in particular, not higher than 210° C., more preferably 180 to 203° C. in case of an interesterification reaction system of behenic acid ester and oleic acid ester. When distillation conditions are selected in this way, formation of undesirable by-products such as high boiling point components due to migration of triglycerides and diglycerides can be prevented. In addition, since heat history becomes lower, deterioration of color and lowering of stability to deterioration by oxidation can also be prevented. These advantages are most remarkable when using the feedstock fatty reactant having a longer fatty acid chain, in particular, that having 22 or more carbon atoms, preferably, 22 to 24 carbon atoms.

Almost all the fatty acids and/or esters liberated from triglycerides are distilled off and then distillation is terminated. After distillation, the reaction mixture as such or, if necessary, with addition of the additional feedstock fatty reactant, is adjusted to a suitable reaction temperature, for example, in case of an interesterification reaction system of behenic acid ester and oleic acid ester, a temperature at which the reaction mixture is stably maintained in a solution state (e.g., at lowest 53 to 54° C.) and the interesterification reaction and distillation steps of the next stage are carried out. In case of obtaining a higher concentration of the specific triglyceride molecular species, if necessary, the number of stages can be increased to further repeat the interesterification reaction and distillation steps.

After completion of the reaction step of the final stage, substantially all the fatty reactant including fatty acids and/or esters liberated from triglycerides are distilled off by conventional distillation to obtained the desired triglycerides.

According to the above process of the present invention, a reaction efficiency of the feedstock fatty reactant can be increased and a concentration of the desired specific triglyceride molecular species can be efficiently increased. In addition, since fractionation of fats and oils such as solvent fractionation is not required in the process of the present invention, the process is useful from a safety viewpoint.

The following Examples and Comparative Examples further illustrate the present invention in detail but are not to be construed to limit the scope thereof. In the following Examples and Comparative Examples, all "parts" and "percents" are by weight unless otherwise stated.

EXAMPLE 1

A commercially available lipase (20 parts; originating in *Rhizopus niveus*; 3,000 IU/ml) was dissolved in cold water (80 parts) and mixed with Cerite (75 parts). The mixture was dried at 20° C. for 4 days to obtain a lipase preparation having water content of not more than 2.0%.

High oleic sunflower oil (28 parts) and ethyl behenate (72 parts) were mixed and to the mixture was added acid clay (2 parts). The resultant mixture was stirred at 110° C. for 20 minutes under reduced pressure of 5 Torr and filtered to obtain a reaction substrate having water content of not more than 50 ppm.

The above-prepared lipase preparation (90 g) was packed in a column and the reaction substrate was passed through the column at 53° C. at a flow rate of 50 g/hr. to effect the interesterification reaction and then the reaction mixture was collected as the 1st stage reaction mixture. The 1st stage reaction mixture was placed in a distillation flask and maintained at 206° C. under reduced pressure of 2 Torr to distill off substantially all ethyl oleate to selectively remove a fraction (51.4 parts). Fatty acid compositions (%) of esters before distillation, esters in the distillate and esters remaining in the flask are shown in Table 1.

TABLE 1

|  | Before distillation | Distillate | Remaining in flask |
| --- | --- | --- | --- |
| C14 | 0.0 | 0.0 | 0.0 |
| C16 | 1.2 | 2.3 | 0.0 |
| C18 | 2.1 | 4.1 | 0.0 |
| C18:1 | 16.3 | 31.6 | 0.0 |
| C18:2 | 0.9 | 1.7 | 0.0 |
| C18:3 | 0.1 | 0.2 | 0.0 |
| C20 | 7.2 | 5.4 | 9.0 |
| C22 | 70.4 | 53.2 | 88.6 |
| C24 | 1.9 | 1.4 | 2.4 |

Then, ethyl behenate (58.2 parts) was added to the mixture (48.6 parts) of the triglycerides and ethyl ester remaining in the flask. According to the same manner as described above, the mixture was treated with acid clay and passed through the column to obtain the 2nd stage reaction mixture. The 2nd stage reaction mixture was maintained at 255° C. under reduced pressure of 2 Torr to completely remove the ester component. The resultant reaction product contained 62% of BOB (1,3-dibehenic-olein) (B: behenic acid as a constituent fatty acid of a triglyceride) and its BBB (tribehen) content was as low as 2.7%. This product had sufficient quality for using as a tempering enhancing material having self-restoration function (i.e., when the material is added to chocolate as its stable crystalline form, the resultant chocolate can restore to the original glossy chocolate even after exposure to high temperatures at which the whole of chocolate is melted, such as body temperature.). The color was 3.0×30 (determined by Lovibond tintometer with a 5+¼ inch cell).

EXAMPLE 2

Palm oil high melting fraction (30 parts, PPP (tripalmitin): 75%, POP (1,3-dipalmito-olein): 25%, P: palmitic acid as a constituent fatty acid of a triglyceride) and ethyl oleate (70 parts, prepared from high oleic sunflower oil) were mixed and dried according to the same manner as that described in Example 1 to obtain a reaction substrate.

According to the same manner as that described in Example 1, the interesterification reaction of the 1st stage was carried out except that Lipozyme (an enzyme manufactured by Novo) was used as a commercially available lipase and the reaction substrate was passed through the column at 55° C. Then, distillation was carried out in a distillation flask by maintaining at 160° C. under reduced pressure of 2 Torr to distill off a fraction (40 parts) to leave only a fraction of the oil and oleic acid ethyl ester.

Then, ethyl oleate (40 parts) was added to the mixture (60 parts) of the triglycerides and ethyl ester remaining in the flask. According to the same manner as that of the 1st stage, the mixture was treated by acid clay and passed through the column to obtain the 2nd stage reaction mixture. This was maintained at 235° C. under reduced pressure of 2 Torr to completely remove the ester component. The resultant reaction product contained 45% of OPO (1,3-dioleo-palmitin)

and sufficient color and stability to deterioration by oxidation (color determined by the above-described method: 1.0×10, AOM: 100 hours).

EXAMPLE 3

According to the same manner as that described in Example 1, trilaurin (manufactured by Sigma, 50 parts, purity: 98%) and stearic acid (50 parts) were mixed to prepare a reaction substrate. The 1st stage interesterification reaction was carried out according to the same manner as that described in Example 1 except that Lipozyme (an enzyme manufactured by Novo) was used as a commercially available lipase, 5 g of it was packed in a column and the reaction substrate was passed through the column at 65° C. at a flow rate of 3 g/hr. Then, the reaction mixture was maintained in a distillation flask at 150° C. under reduced pressure of 2 Torr to remove a fraction rich in lauric acid.

Then, stearic acid (25 parts) was added to the mixture (75 parts) of the triglycerides and fatty acids remaining in the flask. According to the same manner as that of the 1st stage, the mixture was treated with acid clay and passed through the column to obtain the 2nd stage reaction mixture. The 2nd stage reaction mixture was maintained in a distillation flask at 250° C. under reduced pressure of 2 Torr to completely remove the fatty acid component. The reaction product contained 53.5% of SLS (1,3-distearo-laurin) (L: lauric acid as a constituent fatty acid of a triglyceride) and had sufficient color and stability to deterioration by oxidation.

COMPARATIVE EXAMPLE 1

The same reaction mixture as that of the 1st reaction mixture of Example 1 was distilled off at 255° C. to completely remove ethyl ester. Then, ethyl behenate (72 parts) was added to the triglycerides remaining in the flask and the mixture was treated with acid clay and passed through the same column as in Example 1 to obtain the 2nd stage reaction mixture. This was maintained at 255° C. under reduced pressure of 2 Torr to completely remove the ester component. The reaction product contained 62% of BOB (1,3-dibehenic-olein). However, since BBB (tribehen) content was as high as 5.1%, a high melting point fraction had to be removed by fractionation to use it as a tempering enhancing material. Further, it was considerably colored and not desired (color determined by the above-described method: 5.0×50).

COMPARATIVE EXAMPLE 2

According to the same manner as that described in Example 2, interesterification and distillation were carried out except that the 1st stage distillation was carried out at 235° C. and the amount of the additional ethyl oleate was 70 parts. The reaction product contained 45% of OPO (1,3-dioleo-palmitin). However, color and stability to deterioration by oxidation were inferior to the product of Example 2 (color determined by the above-described method: 2.0×20, AOM: 70 hours).

As is seen from the above, in comparison with Comparative Examples, the amounts of the feedstock fatty reactants used in Examples are smaller and formation of by-products is inhibited. Therefore, according to the process of the present invention, a concentration of the desired triglyceride molecular species can efficiently be increased in comparison with conventional multistage interesterification processes.

What is claimed is:

1. A process for producing target triglycerides by interesterification of a first triglyceride having first fatty acids with a second fatty acid having 18 or more carbon atoms or a lower alcohol ester thereof, employing an enzyme catalyst, which process comprises:

a) selecting said first triglyceride having first fatty acids and said second fatty acid or lower alcohol ester thereof so that said first fatty acids or a lower alcohol ester thereof have a boiling point lower than said second fatty acid or a lower alcohol ester thereof, such that only said first fatty acids are selectively distilled off in the following step c), b) subjecting said first triglycerides having first fatty acids to interesterification with said second fatty acid or a lower alcohol ester thereof with an enzyme catalyst whereby there is formed a reaction mixture comprising said target triglycerides having said second fatty acids, said first triglycerides having first fatty acids, said first fatty acids or lower alcohol esters thereof, and said second fatty acid or a lower alcohol ester thereof, c) separating said reaction mixture from said enzyme catalyst and subjecting the separated reaction mixture to distillation whereby said first fatty acid or lower alcohol esters thereof are distilled off, while preventing distilling off of said first triglycerides having first fatty acids and said target triglycerides having said second fatty acids, d) repeating steps b) and c) to increase the concentration of said target triglycerides having second fatty acids, and e) distilling off all remaining fatty acids and lower alcohol esters thereof to recover the target triglyceride product having said second fatty acid.

2. The process of claim 1, wherein the distillation of step c) is carried out at a temperature not higher than 210° C.

3. The process of claim 1, which process consists essentially of steps a. to d.

* * * * *